United States Patent

Gayer et al.

Patent Number: 4,623,655
Date of Patent: Nov. 18, 1986

[54] FUNGICIDAL IMINOMETHYL-AZOLYL DERIVATIVES

[75] Inventors: Herbert Gayer, Monheim; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 676,161

[22] Filed: Nov. 29, 1984

[30] Foreign Application Priority Data

Dec. 20, 1983 [DE] Fed. Rep. of Germany ....... 3345899

[51] Int. Cl.$^4$ ............... A01N 43/50; A01N 43/653; C07D 233/61; C07D 249/08
[52] U.S. Cl. .................... 514/399; 514/184; 514/383; 514/397; 548/109; 548/262; 548/336; 548/341
[58] Field of Search ............ 548/109, 262, 341, 336; 424/245, 269, 273 R; 514/184, 383, 399, 397

[56] References Cited

U.S. PATENT DOCUMENTS

| 4,005,083 | 1/1977 | Buchel et al. ............... 424/273 R |
| 4,359,469 | 11/1982 | Stetter et al. ............... 424/273 R |
| 4,391,804 | 7/1983 | Ohyama et al. ................... 548/341 |

FOREIGN PATENT DOCUMENTS

| 2549899 | 11/1975 | Fed. Rep. of Germany ....... 548/341 |
| 53-65879 | 6/1978 | Japan ................... 548/341 |
| 54-132567 | 10/1979 | Japan ................... 548/341 |

Primary Examiner—Richard A. Schwartz
Assistant Examiner—Kurt G. Briscoe
Attorney, Agent, or Firm—Sprung Horn Kramer & Woods

[57] ABSTRACT

Iminomethyl-azolyl derivatives of the formula

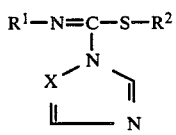

in which
X is nitrogen or a CH group,
$R^1$ is alkyl, alkenyl, alkoxyalkyl, optionally substituted cycloalkyl, or phenyl, phenylalkyl or phenoxyalkyl which is optionally substituted in the phenyl part and
$R^2$ is optionally substituted alkyl, or alkenyl, alkinyl, halogenoalkyl, halogenoalkenyl, cyano, optionally substituted benzyl or phenyl, or a cycloalkyl radical which is optionally substituted by oxygen and/or interrupted by a keto group, or addition products thereof with acids or metal salts with the exception of the compounds in which (a)
X represents a CH group,
$R^1$ represents phenyl which is subsituted by halogen and/or alkyl and
$R^2$ represents alkyl, or (b)
X represents nitrogen or a CH group,
$R^1$ represents phenyl which is optionally substituted by halogen, alkyl, alkoxy and/or trifluoromethyl and
$R^2$ represents benzyl which is optionally substituted by halogen, alkyl, alkoxy and/or trifluoromethyl which possess fungicidal activity. The intermediates wherein $R^2$ is replaced by an alkali metal or alkaline earth metal are also disclosed.

14 Claims, No Drawings

FUNGICIDAL IMINOMETHYL-AZOLYL DERIVATIVES

The invention relates to new iminomethyl-azolyl derivatives, several processes for their preparation and their use as plant protection agents.

It is already known that certain imidazolyl-amidines, such as, for example, 1-(3,4-dichlorophenyl)-1-methyl-2-imidazol-1-yl-3-i-propyl-amidine, 1-phenyl-1-trifluoromethyl-2-(imidazol-1-yl)-3-phenyl-amidine, 1,3-dimethyl-2-(imidazol-1-yl)-1-phenyl-amidine and 1-(2,4-dichlorophenyl)-1-ethyl-2-(imidazol-1-yl)-3-i-propyl-amidine, have good fungicidal properties (compare, for example, DE-OS (German Published Specification) No. 2,549,899, and similar compounds are also known from the Laid-Open Japanese Patent Application Nos. 65 879/1978 and 132,567/1979). However, the action of these compounds is not always completely satisfactory, especially when low amounts and concentrations are applied.

New iminomethyl-azolyl derivatives of the general formula (I)

$$R^1-N=C-S-R^2 \quad (I)$$
(with azolyl ring attached at N, X position)

in which
X represents nitrogen or a CH group,
R$^1$ represents straight-chain or branched alkyl, alkenyl, alkoxyalkyl, optionally substituted cycloalkyl, or phenyl, phenylalkyl or phenoxyalkyl which is optionally substituted in the phenyl part and
R$^2$ represents optionally substituted straight-chain or branched alkyl, or alkenyl, alkinyl, halogenoalkyl, halogenoalkenyl, cyano, optionally substituted benzyl or phenyl, or a cycloalkyl radical which is optionally substituted by oxygen and/or interrupted by a keto group, but wherein it is not possible at the same time for
(a)
X to represent a CH group,
R$^1$ to represent phenyl which is substituted by halogen and/or alkyl and
R$^2$ to represent alkyl, or
(b)
X to represent nitrogen or a CH group,
R$^1$ to represent phenyl which is optionally substituted by halogen, alkyl, alkoxy and/or trifluoromethyl and
R$^2$ to represent benzyl which is optionally substituted by halogen, alkyl, alkoxy and/or trifluoromethyl,
and acid addition salts and metal salt complexes thereof, have now been found.

It has furthermore been found that the new iminomethyl-azolyl derivatives of the formula (I) are obtained by a process in which
(a) if X represents a CH group, isothiocyanates of the formula (II)

$$R^1-N=C=S \quad (II)$$

in which R$^1$ has the abovementioned meaning, is reacted with imidazole in the presence of a strong base and, if appropriate, in the presence of a diluent, and the salts obtained in this manner, of the formula (III)

$$\left[ R^1-N\cdots\overset{S}{\underset{C}{\diagdown}}\cdots \right]^{\ominus} Me^{\oplus} \quad (III)$$
(with imidazolyl ring on C)

in which
R$^1$ has the abovementioned meaning and
Me represents one equivalent of an alkali metal atom or alkaline earth metal atom,
are isolated, if appropriate, and reacted with halides of the formula (IV)

$$R^2Hal \quad (IV)$$

in which
R$^2$ has the abovementioned meaning and
Hal represents halogen,
if appropriate in the presence of a diluent; or in which
(b) if X represents a CH group or nitrogen, isocyanide dihalides of the formula (V)

$$R^1-N=C(Hal^1)_2 \quad (V)$$

in which
R$^1$ has the abovementioned meaning and
Hal$^1$ represents halogen, such as chlorine or bromine, is reacted with imidazole or triazole in the presence of an acid acceptor and, if appropriate, in the presence of a diluent, and the compounds obtained in this manner, of the formula (VI)

$$R^1-N=C\diagup^{Hal^1}_{\diagdown N\cdots} \quad (VI)$$
(with azolyl ring at X, N positions)

in which R$^1$, X and Hal$^1$ have the abovementioned meanings, are isolated, if appropriate, and reacted with thiols of the formula (VII)

$$R^2S-Y \quad (VII)$$

in which
R$^2$ has the abovementioned meaning and
Y represents hydrogen or one equivalent of an alkali metal atom or alkaline earth metal atom,
if appropriate in the presence of an acid acceptor and if appropriate in the presence of diluents.

If appropriate, an acid or a metal salt can then be added onto the compounds of the formula (I) obtained in this manner.

Surprisingly, the compounds according to the invention have a more powerful fungicidal action than the known active compounds 1-(3,4-dichlorophenyl)-1-methyl-2-imidazol-1-yl-3-i-propyl-amidine, 1-phenyl-1-trifluoromethyl-2-(imidazol-1-yl)-3-phenyl-amidine, 1,3-dimethyl-2-(imidazol-1-yl)-1-phenyl-amidine and 1-(2,4-dichlorophenyl)-1-ethyl-2-(imidazol-1-yl)-3-i- propyl-amidine. The active compounds according to the invention thus represent an enrichment of the art.

Formula (I) provides a general definition of the iminomethyl-azolyl derivatives according to the invention.

Preferred compounds of the formula (I) are those in which

X represents nitrogen or a CH group, $R^1$ represents straight-chain or branched alkyl or alkoxyalkyl with in each case 1 to 12 carbon atoms in the alkyl part, or represents alkenyl with up to 4 carbon atoms, or represents cycloalkyl which has 3 to 8 carbon atoms and is optionally monosubstituted or polysubstituted by identical or different halogen and/or alkyl substituents, or represents phenyl, phenylalkyl or phenoxyalkyl, with in each case 1 to 6 carbon atoms in the alkyl part and in each case optionally monosubstituted or polysubstituted by identical or different substituents in the phenyl part, preferred possible substituents on the phenyl in each case being: halogen, such as, in particular, fluorine, chlorine, bromine and/or iodine; alkyl, alkoxy and alkylthio with in each case 1 to 4 carbon atoms in the alkyl part; halogenoalkyl, halogenoalkoxy and halogenoalkylthio with in each case 1 to 4 carbon atoms in the alkyl part and 1 to 5 identical or different halogen atoms, such as fluorine, chlorine and/or bromine; and/or phenoxy; and $R^2$ represents straight-chain or branched alkyl which has 1 to 12 carbon atoms and is optionally monosubstituted or polysubstituted by identical or different substituents, preferred possible substituents on the alkyl being: a phthalimido radical; cyano; halogen, such as fluorine, chlorine, bromine and/or iodine; a cycloalkyl grouping which has 2 to 6 carbon atoms and is optionally interrupted by oxygen; and/or the groupings $R^3O$—, $R^3S$—, $R^3$—CO—O, $R^3O$—CO, $R^3$—CO—, $R^3O$—CO—(CH$_2$)$_n$—CO—, $(R^4O)(R^5O)$—CR$^6$ and $R^7R^8N$—CO—, in which $R^3$, $R^4$ and $R^5$ are identical or different and represent straight-chain or branched alkyl with 1 to 6 carbon atoms, or represent phenyl which is optionally substituted by fluorine, chlorine, methyl, methoxy, methylthio, trifluoromethyl, trifluoromethoxy and/or trifluoromethylthio, or $R^4$ and $R^5$ together represent an alkanediyl radical which has 2 or 3 carbon atoms and is optionally substituted by fluorine and/or chlorine, n represents the number 0 or 1 and $R^6$, $R^7$ and $R^8$ are identical or different and represent hydrogen, straight-chain or branched alkyl with 1 to 4 carbon atoms, or phenyl which is optionally substituted by fluorine, chlorine, methyl, methoxy, methylthio, trifluoromethyl, trifluoromethoxy and/or trifluoromethylthio; or $R^2$ furthermore preferably represents alkenyl or alkinyl with 3 to 6 carbon atoms; or represents halogenoalkenyl with 3 to 6 carbon atoms in the alkenyl part and 1 to 3 halogen atoms, such as, in particular, chlorine, bromine and/or iodine; or cyano, or optionally substituted benzyl or phenyl, preferred possible substituents on the phenyl being the substituents which have been mentioned as substituents on the phenyl in the description of $R^1$; or represents a cycloalkyl group which has 3 to 6 carbon atoms and is optionally interrupted by oxygen and/or a keto group, but wherein it is not possible at the same time for (a)
X to represent a CH group,
$R^1$ to represent phenyl which is substituted by halogen and/or alkyl and
$R^2$ to represent alkyl, or (b)
X to represent nitrogen or a CH group,
$R^1$ to represent phenyl which is optionally substituted by halogen, alkyl, alkoxy and/or trifluoromethyl and
$R^2$ to represent benzyl which is optionally substituted by halogen, alkyl, alkoxy and/or trifluoromethyl.

Particularly preferred compounds of the formula (I) are those in which

X represents nitrogen or a CH group, $R^1$ represents methyl, ethyl, n-propyl, i-propyl, n-butyl, i-butyl, sec.-butyl, tert.-butyl, pentyl, hexyl, heptyl, octyl, nonyl, decyl, dodecyl, methoxymethyl, methoxyethyl, methoxy-n-propyl, methoxy-i-propyl, methoxy-n-butyl, methoxy-i-butyl, ethoxymethyl, ethoxyethyl, ethoxy-n-propyl, ethoxy-i-propyl, ethoxy-n-butyl, ethoxy-i-butyl, n-propoxymethyl, n-propoxyethyl, n-propoxy-n-propyl, n-propoxy-i-propyl, n-propoxy-n-butyl, n-propoxy-i-butyl, i-propoxymethyl, i-propoxyethyl, i-propoxy-n-propyl, i-propoxy-i-propyl, i-propoxy-n-butyl, i-propoxy-i-butyl, n-butoxymethyl, n-butoxyethyl, n-butoxy-n-propyl, n-butoxy-i-propyl, n-butoxy-n-butyl, n-butoxy-i-butyl, i-butoxymethyl, i-butoxyethyl, i-butoxy-n-propyl, i-butoxy-i-propyl, i-butoxy-n-butyl, i-butoxy-i-butyl, cyclopropyl, cyclopentyl or cyclohexyl, or represents cyclohexyl which is optionally mono-, di- or tri-substituted by identical or different substituents from the group comprising fluorine, chlorine, bromine, methyl, ethyl, n-propyl, i-propyl, n-butyl, i-butyl, sec.-butyl and/or tert.-butyl, or represents phenyl, benzyl, phenethyl, benzyloxy or phenethoxy, each of which is optionally mono-, di- or tri-substituted in the phenyl part by identical or different substituents from the group comprising fluorine, chlorine, bromine, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.-butylthio, tert.-butylthio, phenoxy, trifluoromethyl, trifluoromethoxy and/or trifluoromethylthio, and $R^2$ represents methyl, ethyl, n-propyl, i-propyl, n-butyl, i-butyl, sec.-butyl, tert.-butyl, pentyl, hexyl, heptyl, octyl, nonyl, decyl or dodecyl, each of which is optionally mono- or di-substituted, preferred possible substituents being: a phthalimido radical, cyano, fluorine, chlorine, bromine, cyclopentyl, cyclohexyl, 2-oxiranyl, 2-tetrahydrofuranyl, 2-tetrahydropyranyl and/or the groupings $R^3O$—, $R^3S$—, $R^3$—CO—O—, $R^3O$—CO—, $R^3$—CO—, $R^3O$—CO—(CH$_2$)$_n$—CO—, $(R^4O)(R^5O)CR^6$— and $R^7R^8N$—CO—, in which $R^3$, $R^4$ and $R^5$ are identical or different and represent methyl, ethyl, n-propyl, i-propyl, n-butyl, i-butyl, sec.-butyl or tert.-butyl, or represent phenyl which is optionally substituted by fluorine, chlorine, methyl, methoxy, trifluoromethyl and/or trifluoromethoxy, or $R^4$ and $R^5$ together represent an alkanediyl radical with 2 or 3 carbon atoms, n represents the number 0 or 1 and $R^6$, $R^7$ and $R^8$ are identical or different and represent hydrogen, methoxy, ethyl, n-propyl, i-propyl, n-butyl, i-butyl, sec.-butyl or tert.-butyl, or represent phenyl which is optionally substituted by fluorine, chlorine, methyl, methoxy, trifluoromethyl and/or trifluoromethoxy; or $R^2$ furthermore represents 2-propen-1-yl, 2-buten-1-yl, 2-methyl-2propen-1-yl, 3-methyl-2-buten-1-yl, 2-propin-1yl, 2-butin-1-yl, 3-methyl-2-butin-1-yl, 3-chloro-2-buten-1-yl, 3-bromo-2-buten-1-yl or cyano, or represents benzyl or phenyl which is optionally substituted by fluorine, chlorine, bromine, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.-butylthio, tert.-butylthio, trifluoromethyl, trifluoromethoxy and/or trifluoromethylthio, or represent cyclohexyl, cyclopentyl, 2-oxo-cyclohexyl, 2-oxo-cyclopentyl, 2-oxo-tetrahydrofuran-3-yl or 2-oxo-tetrahydropyran-3-yl, but wherein it is not possible at the same time for (a)

X to represent a CH group, $R^1$ to represent phenyl which is substituted by halogen and/or alkyl and $R^2$ to represent alkyl, or (b)

X to represent nitrogen or a CH group, $R^1$ to represent phenyl which is optionally substituted by halogen, alkyl, alkoxy and/or trifluoromethyl and $R^2$ to represent benzyl which is optionally substituted by halogen, alkyl, alkoxy and/or trifluoromethyl.

Other compounds of the general formula (I) which are also particularly preferred are those in which X represents nitrogen or the CH group, $R^1$ represents alkyl with 1 to 12 carbon atoms, alkenyl with up to 4 carbon atoms, cycloalkyl with 5 or 6 carbon atoms, it being possible for the latter to be substituted by 1 to 3 alkyl groups with up to 3 carbon atoms, or, finally, phenyl, phenylalkyl or phenoxyalkyl with in each case up to 4 carbon atoms in the alkyl part, it being possible for the last three groups mentioned to be mono-, di- or tri-substituted in the phenyl part by halogen, alkyl, alkoxy and alkylthio with in each case 1 to 3 carbon atoms, and/or by halogenoalkyl with up to 2 carbon atoms and up to 5 halogen atoms, such as, in particular, trifluoromethyl, and $R^2$ represents alkenyl or alkinyl with 3 to 4 carbon atoms, it being possible for the last two radicals mentioned to carry 1 to 3 halogen atoms, or, furthermore, represents cyano, cyclohexylmethyl or phenyl, it being possible for the last radical mentioned to be substituted by the substituent on phenyl mentioned in the case of $R^1$, or, finally, represents a cycloalkyl group with 3 to 6 carbon atoms, in which oxygen or a carbonyl group can be inserted in the ring system, or, furthermore, for the case where (a)

X does not represent a CH group at the same time as $R^1$ represents phenyl which is substituted by halogen and/or alkyl, $R^2$ can also additionally represent primary, secondary or tertiary alkyl with up to 12 carbon atoms, which can be substituted by halogen, cyano and a phthalimido radical, by alkoxy and alkylthio radicals with in each case up to 3 carbon atoms, and by alkylcarbonyl, alkoxycarbonyl and alkylcarbonyloxy with in each case up to 4 carbon atoms in the alkyl parts, or, finally, for the case where (b)

X does not represent nitrogen or a CH group at the same time as $R^1$ represents phenyl which is optionally substituted by halogen, alkyl, alkoxy and/or trifluoromethyl, $R^2$ also additionally represents benzyl, which can be substituted in the phenyl part by the substituents on phenyl mentioned in the case of $R^1$.

Addition products of acids and those iminomethyl-azolyl derivatives of the formula (I) in which the substituents $R^1$, $R^2$ and X have the meanings which have already been mentioned as preferred for these substituents are also preferred compounds according to the invention.

Preferred acids which can be added on include hydrogen halide acid, such as, for example, hydrochloric acid and hydrobromic acid, in particular hydrochloric acid, and furthermore phosphoric acid, nitric acid, monofunctional and bifunctional carboxylic acids and hydrocarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II to IV and sub-groups I and II and IV to VIII and those iminomethyl-azolyl derivatives of the formula (I) in which the substituents $R^1$, $R^2$ and X have the meanings which have already been mentioned as preferred for these substituents are also preferred compounds according to the invention.

Salts of copper zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, nitric acid and sulphuric acid.

The following compounds of the general formula (I) may be mentioned specifically, in addition to the compounds mentioned in the preparation examples:

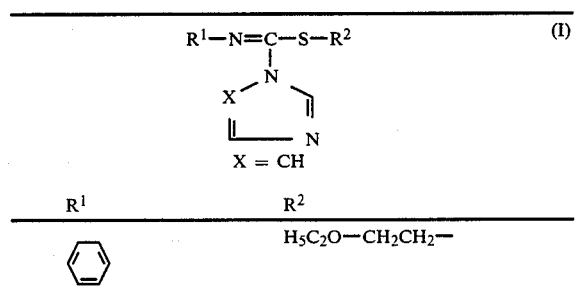

-continued $$R^1-N=C-S-R^2 \quad (I)$$
with N-CH=X ring, X = CH

| R¹ | R² |
|---|---|
| C₆H₅ (phenyl) | H₃CO—CH₂CH₂— |
| C₆H₅ | H₅C₂S—CH₂CH₂— |
| C₆H₅ | H₃CS—CH₂CH₂— |
| C₆H₅ | H₂C=CH—CH₂— |
| C₆H₅ | H₃C—CH=CH—CH₂— |
| 4-Cl, 2-CF₃-C₆H₃— | H₅C₂O—CH₂CH₂— |
| 4-Cl, 2-CF₃-C₆H₃— | H₃CO—CH₂CH₂— |
| 4-Cl, 2-CF₃-C₆H₃— | H₅C₂S—CH₂CH₂— |
| 4-Cl, 2-CF₃-C₆H₃— | H₃CS—CH₂CH₂— |
| 4-Cl, 2-CF₃-C₆H₃— | H₂C=CH—CH₂— |
| 4-Cl, 2-CF₃-C₆H₃— | H₃C—CH=CH—CH₂— |
| 4-Cl-C₆H₄— | H₅C₂O—CH₂CH₂— |
| 4-Cl-C₆H₄— | H₃CO—CH₂CH₂— |
| 4-Cl-C₆H₄— | H₅C₂S—CH₂CH₂— |
| 4-Cl-C₆H₄— | H₃CS—CH₂CH₂— |
| 4-Cl-C₆H₄— | H₂C=CH—CH₂— |
| 4-Cl-C₆H₄— | H₃C—CH=CH—CH₂— |
| 4-Cl-C₆H₄— | H₅C₂O—CH₂—CH₂— |
| 2,4-Cl₂-C₆H₃— | H₃CO—CH₂CH₂— |
| 2,4-Cl₂-C₆H₃— | H₅C₂S—CH₂CH₂— |
| 2,4-Cl₂-C₆H₃— | H₃CS—CH₂CH₂— |
| 2,4-Cl₂-C₆H₃— | H₃C—CH=CH—CH₂— |
| 2,4-Cl₂-C₆H₃— | H₂C=CH—CH₂— |
| cyclohexyl | H₅C₂O—CH₂CH₂— |
| cyclohexyl | H₃CO—CH₂CH₂— |
| cyclohexyl | H₅C₂S—CH₂CH₂— |
| cyclohexyl | H₃CS—CH₂CH₂— |
| cyclohexyl | H₃C—CH=CH—CH₂— |
| 4-H₃C-C₆H₄— | H₅C₂O—CH₂CH₂— |
| 4-H₃C-C₆H₄— | H₃CO—CH₂CH₂— |

-continued $$R^1-N=C-S-R^2 \quad (I)$$

with ring: X-N, X=CH, =N

X = CH

| $R^1$ | $R^2$ |
|---|---|
| 4-H₃C-C₆H₄- | H₅C₂S—CH₂CH₂— |
| 4-H₃C-C₆H₄- | H₃CS—CH₂CH₂— |
| 4-H₃C-C₆H₄- | H₂C=CH—CH₂— |
| 4-H₃C-C₆H₄- | H₃C—CH=CH—CH₂— |
| 3-CF₃-C₆H₄- | H₅C₂O—CH₂CH₂— |
| 3-CF₃-C₆H₄- | H₃CO—CH₂CH₂— |
| 3-CF₃-C₆H₄- | H₅C₂S—CH₂CH₂— |
| 3-CF₃-C₆H₄- | H₃CS—CH₂CH₂— |
| 3-CF₃-C₆H₄- | H₂C=CH—CH₂— |
| 3-CF₃-C₆H₄- | H₃C—CH=CH—CH₂— |
| 4-F₃C-C₆H₄- | H₅C₂O—CH₂CH₂— |
| 4-F₃C-C₆H₄- | H₃CO—CH₂CH₂— |
| 4-F₃C-C₆H₄- | H₅C₂S—CH₂CH₂— |
| 4-F₃C-C₆H₄- | H₃CS—CH₂CH₂— |
| 4-F₃C-C₆H₄- | H₃C—CH=CH—CH₂— |
| 4-F₃C-C₆H₄- | H₂C=CH—CH₂— |
| 3-Cl-C₆H₄- | H₅C₂O—CH₂CH₂— |
| 3-Cl-C₆H₄- | H₃CO—CH₂CH₂— |
| 3-Cl-C₆H₄- | H₅C₂S—CH₂CH₂— |
| 3-Cl-C₆H₄- | H₃CS—CH₂CH₂— |
| 3-Cl-C₆H₄- | H₃C—CH=CH—CH₂— |
| 3-Cl-C₆H₄- | H₂C=CH—CH₂— |
| 3,4-Cl₂-C₆H₃- | H₅C₂O—CH₂CH₂— |
| 3,4-Cl₂-C₆H₃- | H₃CO—CH₂CH₂— |
| 3,4-Cl₂-C₆H₃- | H₅C₂S—CH₂CH₂— |
| 3,4-Cl₂-C₆H₃- | H₃CS—CH₂CH₂— |
| 3,4-Cl₂-C₆H₃- | H₃C—CH=CH—CH₂— |
| 3,4-Cl₂-C₆H₃- | H₂C=CH—CH₂— |

-continued $$R^1-N=C-S-R^2 \quad (I)$$
with N attached to X=CH ring (X=CH)

| $R^1$ | $R^2$ |
|---|---|
| H₃CO—C₆H₄— | $H_5C_2O-CH_2CH_2-$ |
| H₃CO—C₆H₄— | $H_3CO-CH_2CH_2-$ |
| H₃CO—C₆H₄— | $H_5C_2S-CH_2CH_2-$ |
| H₃CO—C₆H₄— | $H_3CS-CH_2CH_2-$ |
| H₃CO—C₆H₄— | $H_3C-CH=CH-CH_2-$ |
| H₃CO—C₆H₄— | $H_2C=CH-CH_2-$ |
| 2,4,6-Cl₃C₆H₂— | $H_5C_2O-CH_2CH_2-$ |
| 2,4,6-Cl₃C₆H₂— | $H_3CO-CH_2CH_2-$ |
| 2,4,6-Cl₃C₆H₂— | $H_5C_2S-CH_2CH_2-$ |
| 2,4,6-Cl₃C₆H₂— | $H_3CS-CH_2CH_2-$ |
| 2,4,6-Cl₃C₆H₂— | $H_3C-CH=CH-CH_2-$ |
| 2,4,6-Cl₃C₆H₂— | $H_2C=CH-CH_2-$ |
| 2,6-(C₂H₅)₂-cyclohexyl— | $H_5C_2O-CH_2CH_2-$ |

-continued $$R^1-N=C-S-R^2 \quad (I)$$
with X=CH

| $R^1$ | $R^2$ |
|---|---|
| 2,6-(C₂H₅)₂-cyclohexyl— | $H_3CO-CH_2CH_2-$ |
| 2,6-(C₂H₅)₂-cyclohexyl— | $H_5C_2S-CH_2CH_2-$ |
| 2,6-(C₂H₅)₂-cyclohexyl— | $H_3CS-CH_2CH_2-$ |
| 2,6-(C₂H₅)₂-cyclohexyl— | $H_3C-CH=CH-CH_2-$ |
| 2,6-(C₂H₅)₂-cyclohexyl— | $H_2C=CH-CH_2-$ |

TABLE 1.2

| $R^1$ | X = N $R^2$ |
|---|---|
| C₆H₅— | $-CH_3$ |
| C₆H₅— | $-C_2H_5$ |
| C₆H₅— | $-C_3H_7-n$ |
| C₆H₅— | $-C_3H_7-i$ |
| C₆H₅— | $-C_4H_9-n$ |
| C₆H₅— | $-C_4H_9-tert$ |
| C₆H₅— | $-C_5H_{11}-n$ |
| C₆H₅— | $-C_6H_{13}-n$ |

TABLE 1.2-continued
| R¹ | X = N / R² |
|---|---|
|  | —C₈H₁₇—n |
| 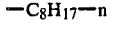 | —C₁₂H₂₅—n |
|  | —CH₂—CH=CH₂ |
| 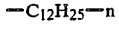 |  |
| 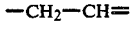 |  |
| 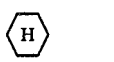 |  |
|  |  |
|  | —CH₃ |
|  | —C₂H₅ |
|  | —C₃H₇—n |
| 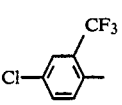 | C₃H₇—i |
| 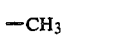 | C₄H₉—n |
| 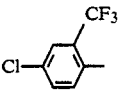 | C₄H₉—tert |
| 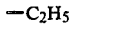 | —C₅H₁₁—n |
| 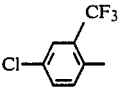 | —C₆H₁₃—n |
| 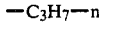 | C₈H₁₇—n |
| 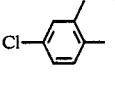 | —C₁₂H₂₅—n |
|  | —CH₂—CH=CH₂ |
| 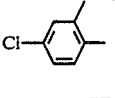 |  |
| 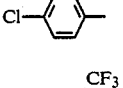 |  |
| 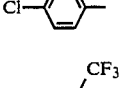 |  |
| 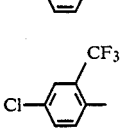 |  |
|  | —CH₃ |
|  | —C₂H₅ |
| 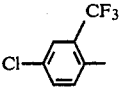 | —C₃H₇—n |
| 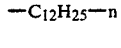 | —C₃H₇—i |
| 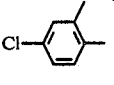 | —C₄H₉—n |
|  | C₄H₉—tert. |
| 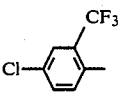 | —C₅H₁₁—n |
|  | —C₆H₁₃—n |
| 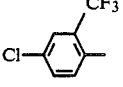 | —C₈H₁₇—n |
|  | —C₁₂H₂₅—n |
| 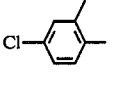 | —CH₂—CH=CH₂ |
| 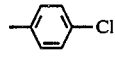 | 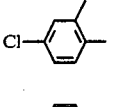 |

TABLE 1.2-continued

| R¹ (X=N) | R² |
|---|---|
| 4-Cl-C₆H₄- | C₆H₅- |
| 4-Cl-C₆H₄- | 4-Cl-C₆H₄- |
| 4-Cl-C₆H₄- | 4-CH₃-C₆H₄- |
| 2,4-Cl₂-C₆H₃- | —CH₃ |
| 2,4-Cl₂-C₆H₃- | —C₂H₅ |
| 2,4-Cl₂-C₆H₃- | —C₃H₇—n |
| 2,4-Cl₂-C₆H₃- | —C₃H₇—i |
| 2,4-Cl₂-C₆H₃- | —C₄H₉—n |
| 2,4-Cl₂-C₆H₃- | —C₄H₉—tert. |
| 2,4-Cl₂-C₆H₃- | —C₅H₁₁—n |
| 2,4-Cl₂-C₆H₃- | —C₆H₁₃—n |
| 2,4-Cl₂-C₆H₃- | —C₈H₁₇—n |
| 2,4-Cl₂-C₆H₃- | —C₁₂H₂₅—n |
| 2,4-Cl₂-C₆H₃- | —CH₂—CH=CH₂ |
| 2,4-Cl₂-C₆H₃- | cyclohexyl |
| 2,4-Cl₂-C₆H₃- | C₆H₅- |
| 3,4-Cl₂-C₆H₃- | 4-Cl-C₆H₄- |
| 3,4-Cl₂-C₆H₃- | 4-CH₃-C₆H₄- |
| 2,4,5-Cl₃-C₆H₂- | —CH₃ |
| 2,4,5-Cl₃-C₆H₂- | —C₂H₅ |
| 2,4,5-Cl₃-C₆H₂- | —C₃H₇—n |
| 2,4,5-Cl₃-C₆H₂- | —C₃H₇—i |
| 2,4,5-Cl₃-C₆H₂- | —C₄H₉—n |
| 2,4,5-Cl₃-C₆H₂- | —C₄H₉—tert. |
| 2,4,5-Cl₃-C₆H₂- | —C₅H₁₁—n |
| 2,4,5-Cl₃-C₆H₂- | —C₆H₁₃—n |
| 2,4,5-Cl₃-C₆H₂- | —C₈H₁₇—n |

TABLE 1.2-continued

| R¹ | X = N / R² |
|---|---|
| 2,4,6-trichlorophenyl | —C₁₂H₂₅—n |
| 2,4,6-trichlorophenyl | —CH₂—CH=CH₂ |
| 2,4,6-trichlorophenyl | cyclohexyl (H) |
| 2,4,6-trichlorophenyl | phenyl |
| 2,4,6-trichlorophenyl | 4-chlorophenyl |
| 2,4,6-trichlorophenyl | 4-methylphenyl |
| 2,6-diethylcyclohexyl | —CH₃ |
| 2,6-diethylcyclohexyl | —C₂H₅ |
| 2,6-diethylcyclohexyl | —C₃H₇—n |
| 2,6-diethylcyclohexyl | —C₃H₇—i |
| 2,6-diethylcyclohexyl | —C₄H₉—n |
| 2,6-diethylcyclohexyl | —C₄H₉—tert. |
| 2,6-diethylcyclohexyl | —C₅H₁₁—n |
| 2,6-diethylcyclohexyl | —C₆H₁₃—n |
| 2,6-diethylcyclohexyl | —C₈H₁₇—n |
| 2,6-diethylcyclohexyl | —C₁₂H₂₅—n |
| 2,6-diethylcyclohexyl | —CH₂—CH=CH₂ |
| 2,6-diethylcyclohexyl | cyclohexyl (H) |
| 2,6-diethylcyclohexyl | phenyl |
| 2,6-diethylcyclohexyl | 4-chlorophenyl |
| 2,6-diethylcyclohexyl | 4-methylphenyl |

If, for example, phenyl isothiocyanate, imidazole and ethoxyethyl chloride are used as starting substances for process (a), the course of the reaction can be represented by the following equation:

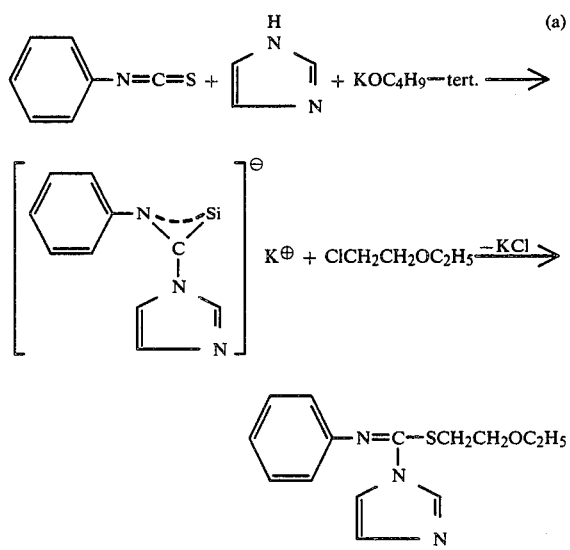

If, for example, 4-chlorophenyl isocyanide dichloride, triazole and n-butanethiol are used as starting substances for process (B) according to the invention, the course of the reaction can be represented by the following equation:

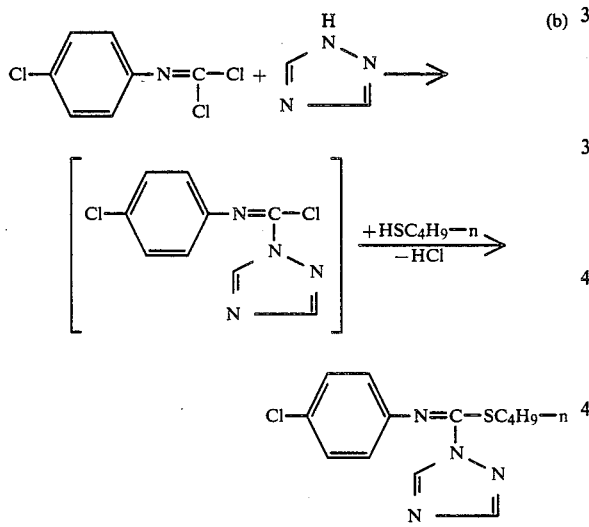

Formula (II) provides a general definition of the isothiocyanates required as starting substances in carrying out process (a) according to the invention. In this formula, $R^1$ has the meaning which has already been mentioned as preferred for this substituent in connection with the description of the substances of the formula (I) according to the invention.

The isothiocyanates of the formula (II) are known compounds of organic chemistry (compare, for example, Houben-Weyl-M/ ller, 4th edition, Volume IX, page 867 et seq., Georg Thieme Verlag, Stuttgart, New York).

Formula (III) provides a general definition of the salts which are formed as intermediates in carrying out process (a) according to the invention and can be isolated, if appropriate. In this formula, $R^1$ has the meaning which has already been mentioned as preferred for this substituent in connection with the description of the substances of the formula (I) according to the invention. Me in this formula represents one equivalent of an alkali metal atom or alkaline earth metal atom, such as sodium, potassium, lithium, magnesium or calcium, preferably sodium or potassium.

The compounds of the formula (III) are new and can be prepared by methods which are known per se, for example by reacting imidazole with isothiocyanates of the formula (II)

$$R^1-N=C=S \quad (II)$$

in which $R^1$ has the abovementioned meaning, in the presence of a strong base, such as, for example, potassium tert.-butylate, and if appropriate in the presence of diluents, such as, for example, tetrahydrofuran, at temperatures between $-20°$ C. and $+150°$ C., preferably between $0°$ C. and $100°$ C. The compounds of the formula (III) obtained in this manner can be isolated by customary methods or can be further reacted with the halides of the formula (IV) according to process (a) to give the compounds of the formula (I) according to the invention.

Formula (IV) provides a general definition of the halides also to be used as starting substances for process (a). In this formula, $R^2$ has the meaning which has already been mentioned as preferred for this substituent in connection with the description of the substances of the formula (I) according to the invention.

Hal in this formula represents halogen, such as chlorine, bromine or iodine, preferably chlorine or bromine.

The halides of the formula (IV) are generally known compounds of organic chemistry.

Formula (V) provides a definition of the dihalides required as starting substances in carrying out process (b) according to the invention. In this formula, $R^1$ has the meaning which has already been mentioned as preferred for this substituent in connection with the description of the substances of the formula (I) according to the invention.

$Hal^1$ in this formula represents halogen, such as chlorine, bromine or iodine, preferably chlorine or bromine.

The compounds of the formula (V) are generally known compounds of organic chemistry.

Formula (VI) provides a general definition of the intermediates which can be isolated, if appropriate, in process (b) according to the invention. In this formula, $R^1$ and X have the meanings which have already been mentioned as preferred for these substituents in connection with the description of the substances of the formula (I) according to the invention. $Hal^1$ in this formula represents halogen, such as chlorine, bromine or iodine, preferably chlorine or bromine.

The compounds of the formula (VI) are known (in this context, compare Derwent references 52 431 A 29 of JP-OS (Japanese Published Specification) No. 53,065,879 and 85 103 B 47 of JP-OS (Japanese Published Specification) No. 54,132,567).

Formula (VII) provides a general definition of the thiols also to be used as starting substances for process (b). In this formula, $R^2$ has the meaning which has already been mentioned as preferred for these substituents in connection with the description of the substances of the formula (I) according to the invention.

Y in this formula represents hydrogen or one equivalent of an alkali metal atom or alkaline earth metal atom, such as sodium, potassium or calcium. Y preferably represents hydrogen.

The compounds of the formula (VII) and their salts are known compounds of organic chemistry.

Possible diluents in the process (variants (a) and (b) according to the invention are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone.

Acid acceptors which can be used for process variants (a) and (b) are virtually all the acid-binding agents which can customarily be employed. These include, in particular: alkali metal hydroxides and oxides and alkaline earth metal hydroxides and oxides, such as sodium hydroxide, potassium hydroxide and, in particular, lithium hydroxide, as well as calcium oxide or calcium hydroxide, alkali metal carbonates and alkaline earth metal carbonates, such as sodium carbonate, potassium carbonate and calcium carbonate, alkali metal alcoholates, such as sodium methylate, ethylate and tert.-butylate and potassium methylate, ethylate and tert.-butylate, and furthermore aliphatic, aromatic or heterocyclic amines, such as triethylamine, dimethylaniline, dimethylbenzylamine, pyridine, diazabicyclooctane and diazabicycloundecene.

The reaction temperature for the reaction according to processes (a) and (b) can be varied within a substantial range. In general, the reactions are carried out at temperatures between $-20°$ C. and $+150°$ C., preferably at $-5°$ C. to $+120°$ C.

Processes (a) and (b) according to the invention are in general carried out under normal pressure.

In carrying out process (a) according to the invention, equimolar amounts of imidazole, base and isothiocyanate are usually employed, and the compounds of the formula (III) obtained in this manner are reacted with 1 mole of halide of the formula (IV), if appropriate after isolation.

In carrying out process (b) according to the invention, equimolar amounts of imidazole or triazole, base and dihalide of the formula (V) are usually employed, and the compounds of the formula (VI) obtained in this manner are reacted with 1 mole of thiol of the formula (VII), or salt thereof, and 1 mole of base, if appropriate after isolation.

The compounds of the formula (I) are worked up by customary methods. They are characterized by their $^1$H-NMR spectra and/or their boiling point.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds of the formula (I), at the concentrations required for combating plant diseases, permits treatment of aboveground parts of plants, of vegetative propagation stock and seeds, and of the soil.

As plant protection agents, the active compounds can be used with good success for combating plant diseases in rice plantations, such as, for example, *Pyricularia oryzae* and *Pellicularia sasakii*, cereal diseases, such as, for example, brown rust on wheat (*Puccinia recondita*), powdery mildew (*Erysiphe graminis*), *Cochliobolus sativus* and *Pyrenophora teres*, apple scab (*Venturia inaequalis*), powdery mildew on apples or Oomycetes.

The active compounds according to the invention also have a broad fungicidal action in the agar plate test.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous as normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

USE EXAMPLES:

The compounds shown below are used as comparison compounds in the use examples which follow:

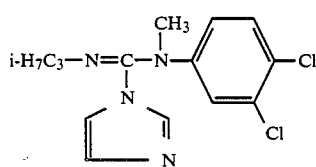
(A)

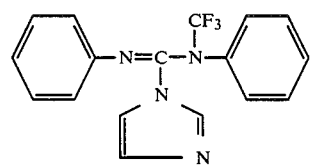
(B)

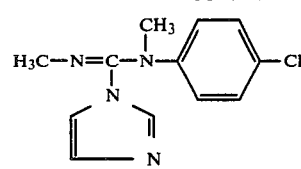
(C)

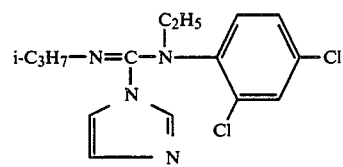
(D)

EXAMPLE A

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 1, 59, 12 13, 14 and 15.

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1 and 28.

EXAMPLE C

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective active, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 17, 47 and 9.

EXAMPLE D

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 28 and 12.

Preparation Examples

EXAMPLE 1

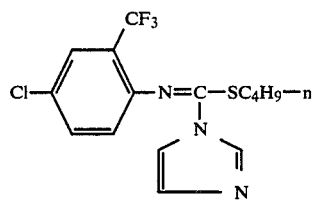

(Process a)

112.2 g (1 mole) of potassium tert.-butylate in 500 ml of absolute tetrahydrofuran are added dropwise to 68 g (1 mole) of imidazole in 500 ml of absolute tetrahydrofuran at 20° C., with cooling. 237.6 g (1 mole) of 2-trifluoromethyl-4-chlorophenyl isothiocyanate in 500 ml of absolute tetrahydrofuran are added dropwise to the sludge-like suspension of the imidazole potassium salt at 0° C. After the addition, a clear solution is formed, and 137 g (1 mole) of n-butyl bromide are added at 0° C. The reaction mixture is stirred for a further 24 hours at 20° C. It is then concentrated and the residue is extracted with ethyl acetate and water. The organic phase is concentrated and the resulting oil is distilled in vacuo.

246 g (68% of theory) of N-[(n-butylthio)-(imidazol-1-yl)-methylidene]-N-(4-chloro-2-trifluoromethylphenyl)-amine of boiling point 155° C. under 0.1 mm Hg are obtained.

EXAMPLE 2

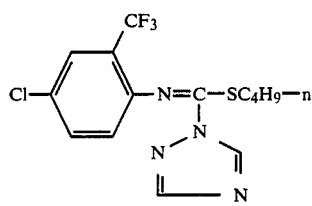

(Process b)

(α) Preparation without isolation of the halide of the formula (VI):

2.8 g (0.04 mole) of triazole and 4.1 g (0.04 mole) of triethylamine are added to 11.1 g (0.04 mole) of 4-chloro-2-trifluoromethyl-phenyl isocyanide dichloride in 40 ml of tetrahydrofuran and the mixture is stirred at 20° C. for one hour. 3.6 g (0.04 mole) of n-butanethiol and 4.1 g (0.04 mole) of triethylamine are then added and the mixture is stirred at 20° C. for one hour. After the solvent has been removed, the residue is taken up in 50 ml of ethyl acetate and 100 ml of water. The organic phase is concentrated and the residue is distilled under a high vacuum.

A fraction with a boiling range up to 140° C./0.5 mm Hg and a second fraction with a boiling range >140° C. 0.5 mm Hg are obtained.

The second fraction is chromatographed on silica gel with an ether/petroleum ether (1:1) mixture. The resulting oil is distilled under a high vacuum in a bulb tube oven.

4.6 g (31% of theory) of N-[(n-butylthio)-(1,2,4-triazol-1-yl)-methylidene)-N-(4-chloro-2-trifluoromethylphenyl)-amine of boiling point 150° C. under 0.5 mm Hg are obtained.

(β) Preparation after isolation of the halide of the formula (VI):

15.5 g (0.05 mole) of N-[(chloro)-(1,2,4-triazol-1-yl)-methylidene]-N-(4-chloro-2-trifluoromethyl-phenyl)-amine in 50 ml of tetrahydrofuran, 4.5 g (0.05 mole) of n-butanethiol and 5.05 g (0.05 mole) of triethylamine are stirred at 20° C. for 25 hours. The solvent is removed and the residue is taken up in ethyl acetate and water. The organic phase is freed from the solvent and then purified under a high vacuum.

12.7 g (70% of theory) of N-[(n-butylthio)-(1,2,4-triazol-1-yl)-methylidene]-N-(4-chloro-2-trifluoromethylphenyl)-amine of boiling point 150° C. to 155° C. under 0.5 mm Hg are obtained.

Starting substance of the formula (VI)

EXAMPLE (VI-1)

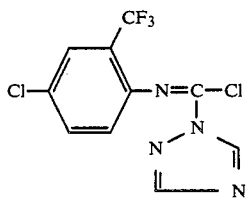

27.6 g (0.1 mole) of 4-chloro-2-trifluoromethylphenyl isocyanide dichloride, 6.9 g (0.1 mole) of triazole and 13.8 g (0.1 mole) of potassium carbonate in 100 ml of acetone are heated under reflux for 24 hours. The reaction mixture is then filtered and freed from the solvent. The residue is taken up in ether and water. After removal of the ether, the organic phase is stirred with 30 ml of petroleum ether, cooled to 0° C. and filtered.

15.8 g (51% of theory) of N-[(chloro)-(1,2,4-triazol-1-yl)-methylidene]-N-(4-chloro-2-trifluoromethyl-phenyl)-amine of melting point 165° C. to 166° C. (toluene) are obtained.

The remaining compounds of the formula (VI) can be obtained according to Example (VI-1).

The following compounds of the general formula (I)

can be prepared by process variants (a) and (b), analogously to Examples 1 and 2:

TABLE 2

| Example No. | X | $R^1$ | $R^2$ | $^1$H—NMR(CDCl$_3$): δ/ppm |
|---|---|---|---|---|
| 3 | CH | n-C$_3$H$_7$ | —H$_2$C—⟨C$_6$H$_4$⟩—Cl | 0.85 (t) [C H$_3$ CH$_2$—CH$_2$—N=] |
| 4 | CH | i-C$_3$H$_7$ | —H$_2$C—⟨C$_6$H$_{11}$⟩H | 1.25 (d) [—SC H$_2$ —⟨⟩ H] |
| 5 | CH | n-C$_6$H$_{13}$ | —CH$_3$ | 0.9 (t) [C H$_3$ (CH$_2$)$_5$—N=] |
| 6 | CH | n-C$_6$H$_{13}$ | —C$_2$H$_5$ | 0.9 (t) [C H$_3$ (CH$_2$)$_5$—N=] |
| 7 | CH | n-C$_6$H$_{13}$ | —C$_3$H$_7$—n | 2.8 (t) [—SC H$_2$ CH$_2$CH$_3$] |
| 8 | CH | n-C$_6$H$_{13}$ | —C$_3$H$_7$—i | 0.95 (t) [C H$_3$ (CH$_2$)$_5$—N=] |
| 9 | CH | n-C$_6$H$_{13}$ | —C$_4$H$_9$—n | 2.8 (t) [—SC H$_2$ CH$_2$CH$_2$CH$_3$] |
| 10 | CH | n-C$_6$H$_{13}$ | —CH$_2$—CH=CH$_2$ | 0.9 (t) [C H$_3$ (CH$_2$)$_5$—N=] |
| 11 | CH | n-C$_6$H$_{13}$ | —CH(CH$_3$)COOCH$_3$ | 0.9 (t) [C H$_3$ (CH$_2$)$_5$—N=] |
| 12 | CH | ⟨C$_6$H$_{11}$⟩H | —CH$_3$ | 2.5 (s) [—SC H$_3$ ] |

TABLE 2-continued

| Example No. | X | R¹ | R² | $^1$H—NMR(CDCl$_3$): δ/ppm |
|---|---|---|---|---|
| 13 | CH | cyclohexyl-H— | —C$_2$H$_5$ | 2.8 (q) [—SCH$_2$CH$_3$] |
| 14 | CH | cyclohexyl-H— | —C$_3$H$_7$—i | 1.25 (d) [(CH$_3$)$_2$CHS—] |
| 15 | CH | cyclohexyl-H— | —C$_4$H$_9$—n | 0.9 (t) [CH$_3$CH$_2$CH$_2$CH$_2$S—] |
| 16 | CH | cyclohexyl-H— | —CH$_2$—cyclohexyl-H | 2.6 (d) [—SCH$_2$—cyclohexyl-H] |
| 17 | CH | cyclohexyl-H— | —CH$_2$—CH=CH$_2$ | 3.2 (d) [—SCH$_2$CH=CH$_2$] |
| 18 | CH | CH$_2$=CH—CH$_2$— | —H$_2$C—C$_6$H$_4$—Cl | 4.0 (s) [—SCH$_2$—C$_6$H$_4$—Cl] |
| 19 | CH | Cl—C$_6$H$_4$—C$_2$H$_4$— | —C$_4$H$_9$—n | 0.8 (t) [CH$_3$(CH$_2$)$_3$—] |
| 20 | CH | Cl—C$_6$H$_4$—C$_2$H$_4$— | —C$_5$H$_{11}$—n | 0.9 (t) [CH$_3$(CH$_2$)$_4$—] |
| 21 | CH | Cl—C$_6$H$_4$—C$_2$H$_4$— | —C$_6$H$_{13}$—n | 0.9 (t) [CH$_3$(CH$_2$)$_5$—] |
| 22 | CH | Cl—C$_6$H$_4$—C$_2$H$_4$— | —C$_{12}$H$_{25}$—n | 0.9 (t) [CH$_3$(CH$_2$)$_{11}$—] |
| 23 | CH | Cl—C$_6$H$_4$—C$_2$H$_4$— | cyclohexyl-H | 3.9 (t) [—CH$_2$CH$_2$N=] |
| 24 | CH | Cl—C$_6$H$_4$—C$_2$H$_4$— | cyclopentyl | 3.9 (t) [—CH$_2$CH$_2$N=] |
| 25 | CH | Cl—C$_6$H$_4$—C$_2$H$_4$— | —H$_2$C—cyclohexyl-H | 2.5 (d) [—SCH$_2$—cyclohexyl-H] |

TABLE 2-continued

| Example No. | X | R¹ | R² | $^1$H—NMR(CDCl$_3$): δ/ppm |
|---|---|---|---|---|
| 26 | CH | 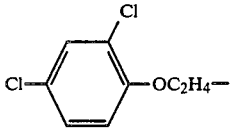 2,4-dichloro-phenyl-OC$_2$H$_4$— | —C$_4$H$_9$—n | 2.8 (t) [—SCH$_2$CH$_2$CH$_2$CH$_3$] |
| 27 | CH |  4-Cl, 2-CF$_3$-phenyl- | —CH$_3$ | 2.3 (s) [CH$_3$S—] |
| 28 | CH | 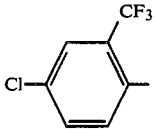 4-Cl, 2-CF$_3$-phenyl- | —C$_2$H$_5$ | 1.2 (t) [CH$_3$CH$_2$S—] |
| 29 | CH |  4-Cl, 2-CF$_3$-phenyl- | —C$_3$H$_7$—n | 0.9 (t) [CH$_3$CH$_2$CH$_2$S—] |
| 30 | CH | 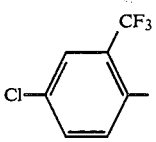 4-Cl, 2-CF$_3$-phenyl- | —C$_3$H$_7$—i | 1.25 (d) [(CH$_3$)$_2$CHS—] |
| 31 | CH |  4-Cl, 2-CF$_3$-phenyl- | —C$_2$H$_4$—N(phthalimido) | 3.3 (t) [—SCH$_2$CH$_2$—] |
| 32 | CH | 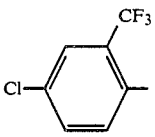 4-Cl, 2-CF$_3$-phenyl- | —C$_4$H$_9$—i | 2.75 (d) [—SCH$_2$CH(CH$_3$)$_2$] |
| 33 | CH |  4-Cl, 2-CF$_3$-phenyl- | —C$_4$H$_9$—sec | 0.85 (t) [CH$_3$—CH$_2$—CH(CH$_3$)—S—] |
| 34 | CH | 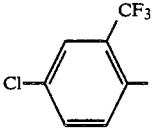 4-Cl, 2-CF$_3$-phenyl- | —C$_4$H$_9$—tert. | 1.45 (s) [(CH$_3$)$_3$CS—] |
| 35 | CH |  4-Cl, 2-CF$_3$-phenyl- | —C$_5$H$_{11}$—n | 2.9 (t) [CH$_3$(CH$_2$)$_3$CH$_2$S—] |

TABLE 2-continued

| Example No. | X | R¹ | R² | ¹H—NMR(CDCl$_3$): δ/ppm |
|---|---|---|---|---|
| 36 | CH | 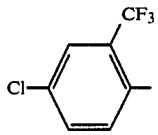 4-Cl, 2-CF$_3$ phenyl | —C$_5$H$_{11}$—sec. | 0.9 (t) [C[H$_3$](CH$_2$)$_2$CH(CH$_3$)—S—] |
| 37 | CH | 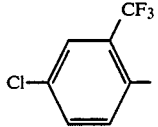 4-Cl, 2-CF$_3$ phenyl | —C$_6$H$_{13}$—n | 2.9 (t) [CH$_3$(CH$_2$)$_4$C[H$_2$]S—] |
| 38 | CH | 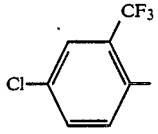 4-Cl, 2-CF$_3$ phenyl | —C$_7$H$_{15}$—n | 2.9 (t) [CH$_3$(CH$_2$)$_5$C[H$_2$]S—] |
| 39 | CH | 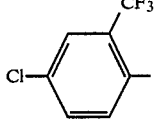 4-Cl, 2-CF$_3$ phenyl | —C$_7$H$_{15}$—sec. | 0.9 (t) [C[H$_3$](CH$_2$)$_4$CH(CH$_3$)S—] |
| 40 | CH | 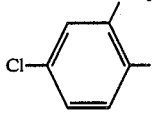 4-Cl, 2-CF$_3$ phenyl | —C$_8$H$_{17}$—n | 2.9 (t) [CH$_3$(CH$_2$)$_6$C[H$_2$]S—] |
| 41 | CH | 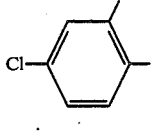 4-Cl, 2-CF$_3$ phenyl | —CH(C$_3$H$_7$-n)(C$_4$H$_9$-n) | 0.7–8.2 (m) [arom. H; heteroarom. H] |
| 42 | CH | 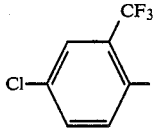 4-Cl, 2-CF$_3$ phenyl | —C$_9$H$_{19}$—n | 2.9 (t) [CH$_3$(CH$_2$)$_7$C[H$_2$]S—] |
| 43 | CH | 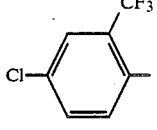 4-Cl, 2-CF$_3$ phenyl | —C$_{12}$H$_{25}$—n | 2.9 (t) [CH$_3$(CH$_2$)$_{10}$C[H$_2$]S—] |
| 44 | CH | 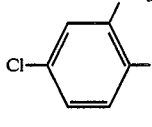 4-Cl, 2-CF$_3$ phenyl |  cyclopentyl | 3.3–3.8 (m) [cyclopentyl-S-H] |
| 45 | CH | 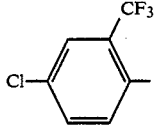 4-Cl, 2-CF$_3$ phenyl | 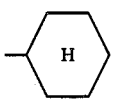 cyclohexyl | 3.0–3.5 (m) [cyclohexyl-S-H] |
| 46 | CH | 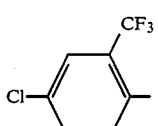 4-Cl, 2-CF$_3$ phenyl | —CH$_2$—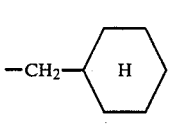 cyclohexyl | 2.75 (d) [—SC[H$_2$]—cyclohexyl] |

TABLE 2-continued

| Example No. | X | R$^1$ | R$^2$ | $^1$H—NMR(CDCl$_3$): δ/ppm |
|---|---|---|---|---|
| 47 | CH | 4-Cl, 2-CF$_3$-phenyl | —CH$_2$—CH=CH$_2$ | 3.45 (d) [—SCH$_2$CH=CH$_2$] |
| 48 | CH | 4-Cl, 2-CF$_3$-phenyl | —CH$_2$—CH=CH—CH$_3$ | 1.60 (d) [CH$_3$—CH=CH—CH$_2$—] |
| 49 | CH | 4-Cl, 2-CF$_3$-phenyl | —CH$_2$—CH=C(Cl)—CH$_3$ | 2.1 (s) [CH$_3$—C(Cl)=] |
| 50 | CH | 4-Cl, 2-CF$_3$-phenyl | —CH$_2$—C(CH$_3$)=CH$_2$ | 1.75 (s) [CH$_3$C(=CH$_2$)CH$_2$S—] |
| 51 | CH | 4-Cl, 2-CF$_3$-phenyl | —CH$_2$—C≡CH | 2.2 (t) [H≡C—CH$_2$—] |
| 52 | CH | 4-Cl, 2-CF$_3$-phenyl | —C$_2$H$_4$—O—C$_2$H$_5$ | 1.1 (t) [CH$_3$CH$_2$O—] |
| 53 | CH | 4-Cl, 2-CF$_3$-phenyl | —CH$_2$—CH(OC$_2$H$_5$)$_2$ | 3.2 (d) [—SCH$_2$CH(OC$_2$H$_5$)$_2$] |
| 54 | CH | 4-Cl, 2-CF$_3$-phenyl | —C(CH$_3$)$_2$—COCH$_3$ | 1.7 (s) [—C(CH$_3$)$_2$—CO—CH$_3$] |
| 55 | CH | 4-Cl, 2-CF$_3$-phenyl | —C$_2$H$_4$—O—COCH$_3$ | 2.0 (s) [CH$_3$—CO—] |
| 56 | CH | 4-Cl, 2-CF$_3$-phenyl | —(CH$_2$)$_4$—O—COCH$_3$ | 2.0 (s) [CH$_3$—CO—O—] |
| 57 | CH | 4-Cl, 2-CF$_3$-phenyl | —C$_2$H$_4$—COOCH$_3$ | 2.0 (s) [CH$_3$OCO—] |

TABLE 2-continued

| Example No. | X | R¹ | R² | ¹H—NMR(CDCl₃): δ/ppm |
|---|---|---|---|---|
| 58 | CH | 4-Cl-2-CF₃-phenyl | γ-butyrolactone (2-yl) | 2.1–2.9 (m) [lactone ring with boxed H's] |
| 59 | CH | 4-Cl-2-CF₃-phenyl | —CH(CH₃)COOCH₃ | 1.65 (d) [—CH(C$\boxed{H_3}$)COOCH₃] |
| 60 | N | 4-Cl-2-CF₃-phenyl | —CH₂—CH=CH₂ | 3.7 (d) [—S—C$\boxed{H_2}$—CH=CH₂] |
| 61 | N | 4-Cl-2-CF₃-phenyl | C₅H₁₁—n | 3.05 (t) [—SC$\boxed{H_2}$(CH₂)₃CH₃] |
| 62 | N | 4-Cl-2-CF₃-phenyl | C₈H₁₇—n | 3.0 (t) [—SC$\boxed{H_2}$(CH₂)₆CH₃] |
| 63 | N | 4-Cl-2-CF₃-phenyl | 4-Cl-phenyl | 7.9 (s) [Triazole—H]<br>8.4 (s) |
| 64 | N | 4-Cl-2-CF₃-phenyl | cyclohexyl (H shown) | 8.0 (s) [Triazole—H]<br>8.5 (s) |
| 65 | N | 4-Cl-2-CF₃-phenyl | C₆H₁₃—n | 3.0 (t) [—SC$\boxed{H_2}$(CH₂)₄CH₃] |
| 66 | N | 4-Cl-2-CF₃-phenyl | C₁₂H₂₅—n | 3.0 (t) [—SC$\boxed{H_2}$(CH₂)₁₀CH₃] |
| 67 | N | 4-Cl-2-CF₃-phenyl | phenyl | 8.0 (s) [Triazole—H]<br>8.5 (s) |

TABLE 2-continued

| Example No. | X | R¹ | R² | ¹H—NMR(CDCl₃): δ/ppm |
|---|---|---|---|---|
| 68 | N | 4-Cl-2-CF₃-phenyl | —C(CH₃)₃ | 1.55 (s) [(CH₃)₃C—] |
| 69 | N | 4-Cl-2-CF₃-phenyl | 4-CH₃-phenyl | 2.25 (s) [—C₆H₄—CH₃] |
| 70 | CH | —CH₂CH₂CH₂OCH₃ | —C₄H₉—n | 3.3 (s) [CH₃O(CH₂)₃—N=] |
| 71 | CH | —CH₂CH₂CH₂OCH₃ | —CH₂-(4-Cl-phenyl) | 3.3 (s) [CH₃O(CH₂)₃—N=] |
| 72 | CH | —CH₂CH₂CH₂OCH₃ | —CH₂-(2,6-diCl-phenyl) | 3.3 (s) [CH₃O(CH₂)₃—N=] |
| 73 | N | 4-Cl-phenyl | —(CH₂)₅—CH₃ | 2.9 (t) [—S—CH₂(CH₂)₄CH₃] |
| 74 | N | 4-Cl-phenyl | —(CH₂)₃—CH₃ | 2.9 (t) [—S—CH₂(CH₂)₂CH₃] |
| 75 | N | 4-Cl-phenyl | —CH₂—CH=CH₂ | 3.65 (d) [—S—CH₂CH=CH₂] |
| 76 | N | 4-Cl-phenyl | 4-Cl-phenyl | bp: 100–107° C. |
| 77 | N | 2,4-diCl-phenyl | —CH₂—CH=CH₂ | 3.5 (d) [—S—CH₂CH=CH₂] |
| 78 | N | 2,4-diCl-phenyl | 4-Cl-phenyl | mp: 100–112° C. |
| 79 | N | 2,4,6-triCl-phenyl | 4-Cl-phenyl | bp: 128–130° C. |

TABLE 2-continued

| Example No. | X | R¹ | R² | ¹H—NMR(CDCl₃): δ/ppm |
|---|---|---|---|---|
| 80 | N |  | 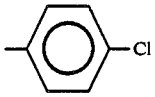 | bp: 78–81° C. |
| 81 | N | 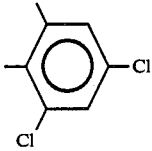 | —CH₂—CH=CH₂ | 3.8 (d) [—S—CH₂CH=CH₂] |
| 82 | N |  | —C₄H₉—n | 2.9 (t) [—S—CH₂CH₂CH₂CH₃] |
| 83 | N |  | —CH₂—CH=CH₂ | 3.55 (d) [—S—CH₂CH=CH₂] |
| 84 | CH |  | —CH₂—CH=CH₂ | 3.4 (d) [—S—CH₂CH=CH₂] |
| 85 | CH |  | —CH₂CH₂OCH₂CH₃ | 1.1 (t) [—S—CH₂—CH₂OCH₂CH₃] |
| 86 | CH |  | —CH₂—CH=CH₂ | 3.7 (d) [—S—CH₂CH=CH₂] |
| 87 | CH |  | —CH₂—CH=CH₂ | 3.4 (d) [—S—CH₂CH=CH₂] |
| 88 | CH |  | —C₄H₉—n | 2.8 (t) [—S—CH₂CH₂CH₂CH₃] |
| 89 | CH | 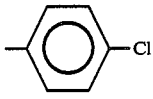 | —(CH₂)₁₁CH₃ | 2.8 (t) [—S—CH₂(CH₂)₁₀CH₃] |
| 90 | CH | —(CH₂)₁₁CH₃ | —CH₂—CH=CH₂ | 3.6 (t) [CH₃(CH₂)₁₀CH₂—N=] |
| 91 | CH |  | —CH₂—CH=CH₂ | 3.4 (d) [—S—CH₂CH=CH₂] |

TABLE 2-continued

| Example No. | X | R¹ | R² | ¹H—NMR(CDCl₃): δ/ppm |
|---|---|---|---|---|
| 92 | CH | —CH(CH₃)—(CH₂)₅CH₃ | —CH₃ | 0.9 (t) [CH₃(CH₂)₅CH(CH₃)—N=] |
| 93 | CH | —CH(CH₃)—(CH₂)₅CH₃ | —C₄H₉—n | 2.8 (t) [—S—CH₂CH₂CH₂CH₃] |
| 94 | CH | —CH(CH₃)—(CH₂)₅—CH₃ | —(CH₂)₁₁CH₃ | 2.8 (t) [—S—CH₂(CH₂)₁₀CH₃] |
| 95 | CH | —(CH₂)₁₁CH₃ | —(CH₂)₁₁CH₃ | 2.7 (t) [—S—CH₂(CH₂)₁₀CH₃] |
| 96 | CH | —(CH₂)₁₁CH₃ | —C₆H₁₃—n | 2.7 (t) [—S—CH₂(CH₂)₄CH₃] |
| 97 | CH | —(CH₂)₁₁CH₃ | —C₄H₉—n | 27 (t) [—S—CH₂CH₂CH₂CH₃] |
| 98 | CH | —(CH₂)₁₁CH₃ | —CH₃ | 37 (t) [CH₃(CH₂)₁₀CH₂—N=] |
| 99 | CH |  | —C₄H₉—n | 27 (t) [—S—CH₂(CH₂)₂CH₃] |
| 100 | CH |  | —CH₂CH₂OCH₃ | 33 (s) [—S—CH₂CH₂OCH₃] |
| 101 | CH | 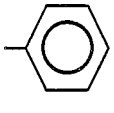 | —C₄H₉—n | 27 (t) [—S—CH₂CH₂CH₂CH₃] |
| 102 | CH |  | —CH₂—CH=CH₂ | 34 (d) [—S—CH₂CH=CH₂] |

It will be understood that the specification and examples are illustrative but not limitative of the present invention and that other embodiments within the spirit and scope of the invention will suggest themselves to those skilled in the art.

We claim:

1. An iminomethyl-imidazolyl derivative of the formula

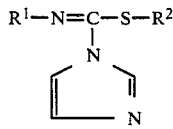

in which

R¹ is phenyl or substituted phenyl selected from

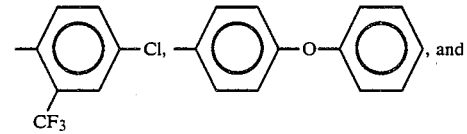, and

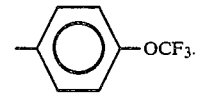.

and

R² is alkyl with 1 to 12 carbon atoms, substituted alkyl with 1 to 12 carbon atoms, the substituents being selected from phthalimido, halogen, cycloalkyl with 3 to 6 carbon atoms, cycloalkyl with 2 to 6 carbon atoms the cycloalkyl ring being interrupted by oxygen, and the groupings R³O—, R³—

CO—O—, R³O—CO, R³—CO— and (R⁴O)(R⁵O)CR⁶, or

R² is alkenyl with 3 to 6 carbon atoms, alkinyl with 3 to 6 carbon atoms, halogenoalkenyl with 3 to 6 carbon atoms and 1 to 3 halogen atoms, or is cycloalkyl with 3 to 6 carbon atoms, or is cycloaklyl with 3 to 6 carbon atoms the cycloalkyl ring being interrupted by oxygen and a keto group, or is phenyl or substituted phenyl, the substituents being selected from halogen and alkyl with 1 to 4 carbon atoms, R³, R⁴ and R⁵ each independently is alkyl with 1 to 6 carbon atoms, and R⁶ is hydrogen or alkyl with 1 to 4 carbon atoms, or an addition product thereof with an acid or metal salt.

2. An iminomethyl-triazolyl derivative of the formula

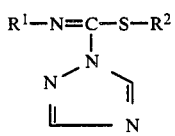

in which

R¹ is phenyl optionally substituted by halogen, alkyl, alkoxy or alkylthio with in each case 1 to 4 carbon atoms in the alkyl part, R² is alkyl with 1 to 12 carbon atoms, substituted alkyl with 1 to 12 carbon atoms, the substituents being selected from phthalimido, halogen, cycloalkyl with 3 to 6 carbon atoms, cycloalkyl with 2 to 6 carbon atoms the cycloalkyl ring being interrupted by oxygen, and the groupings R³O—, R³—CO—O—, R³O—CO, R³—CO— and (R⁴O)(R⁵O)CR⁶, or R² is alkenyl with 3 to 6 carbon atoms, alkinyl with 3 to 6 carbon atoms, halogenoalkenyl with 3 to 6 carbon atoms and 1 to 3 halogen atoms, or is cycloaklyl with 3 to 6 carbon atoms, or is cycloaklyl with 3 to 6 carbon atoms the cycloalkyl ring being interrupted by oxygen and a keto group, or is phenyl or substituted phenyl, the substituents being selected from halogen and alkyl with 1 to 4 carbon atoms, R³, R⁴ and R⁵ each independently is alkyl with 1 to 6 carbon atoms, and R⁶ is hydrogen or alkyl with 1 to 4 carbon atoms, or an addition product thereof with an acid or metal salt.

3. A iminomethyl-azolyl derivative of the formula

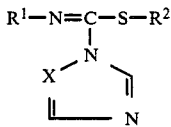

in which

X is nitrogen or a CH group,

R¹ is alkyl or alkoxyalkyl with in each 1 to 12 carbon atoms in the alkyl part, or alkenyl with up to 4 carbon atoms, or cycloalkyl which has 3 to 8 carbon atoms and is optionally substituted by halogen and/or alkyl, or is phenyalkyl or phenoxyalkyl with in each case 1 to 6 carbon atoms in the alkyl part and in each case optionally substituted in the phenyl part by halogen, alkyl, alkoxy or alkylthio with in each case 1 to 4 carbon atoms in the alkyl part, halogenoalkyl, halogenoalkyl or halogenoalkylthio with in each case 1 to 4 carbon atoms in the alkyl part and 1 to 5 identical or different halogen atoms, and/or phenoxy; and R² is benzyl optionally substituted by halogen and/or alkyl with 1 to 4 carbon atoms, or an addition product thereof with an acid or metal salt.

4. A compound according to claim 1, wherein such compound is N-[(n-butylthio)-(imidazol-1-yl)-methylidene]-N-(4-chloro-2-trifluoromethyl-phenyl)-amine of the formula

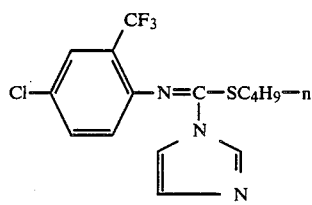

or an addition product thereof with an acid or metal salt.

5. A compound according to claim 1, wherein such compound is N-[(ethylthio)-(imidazol-1-yl)-methylidene]-N-(4-chloro-2-trifluoromethyl-phenyl)-amine of the formula

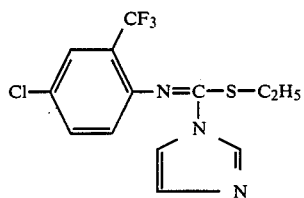

or an addition product thereof with an acid or metal salt.

6. A compound according to claim 1, wherein such compound is N-[(allylthio)-(imidazol-1-yl)-methylidene]-N-(4-chloro-2-trifluoromethyl-phenyl)-amine of the formula

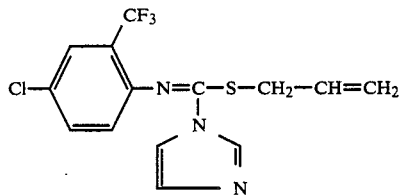

or an addition product thereof with an acid of metal salt.

7. A compound according to claim 1, wherein such compound is N-[(1-carbomethoxyethylthio)-(imidazol-1-yl)-methylidene]-N-(4-chloro-2-trifluoromethyl-phenyl)-amine of the formula

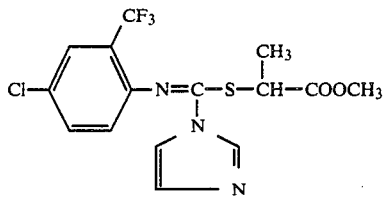

or an addition product thereof with an acid or metal salt.

8. A fungicidal composition comprising a fungicidally effective amount of a compound or addition product according to claim 1 in admixture with a diluent.

9. A fungicidal composition comprising a fungicidally effective amount of a compound or addition product according to claim 2 in admixture with a diluent.

10. A fungicidal composition comprising a fungicidally effective amount of a compound or addition product according to claim 3 in admixture with a diluent.

11. A method of combating fungi which comprises applying to such fungi or to a fungus habitat a fungicidally effective amount of a compound or addition product according to claim 1.

12. A method of combating fungi which comprises applying to such fungi or to a fungus habitat a fungicidally effective amount of a compound or addition product according to claim 2.

13. A method of combating fungi which comprises applying to such fungi or to a fungus habitat a fungicidally effective amount of a compound or addition product according to claim 3.

14. A method of combating fungi which comprises applying to such fungi or to a fungus habitat a fungicidally effective amount of a compound of a compound selected from the group consisting of N-[(n-butylthio)-(imidazol-1-yl)-methylidene]-N-(4-chloro-2-trifluoromethyl-phenyl)-amine, N-[(methylthio)-(imidazol-1-yl)-methylidene)-N-cyclohexylamine, N-[(n-butylthio)-(imidazol-1-yl)-methylidene]-N-cyclohexylamine, N-[(allylthio)-(imidazol-1-yl)-methylidene]-N-cyclohexylamine, N-[(ethylthio)-(imidazol-1-yl)-methylidene]-N-(4-chloro-2-trifluoromethyl-phenyl)-amine, N-[(allylthio)-(imidazol-1-yl)-methylidene]-N-(4-chloro-2-trifluoromethyl-phenyl)-amine, or N-[(1-carbomethoxyethylthio)-(imidazol-1-yl)-methylidene]-N-(4-chloro-2-trifluoromethyl-phenyl)-amine, or an addition product thereof with an acid or metal salt.

* * * * *